ð US010779999B2

(12) United States Patent
Miyama et al.

(10) Patent No.: US 10,779,999 B2
(45) Date of Patent: Sep. 22, 2020

(54) DISPOSABLE ABSORBENT ARTICLE WITH WATER REPELLING LAYER

(71) Applicant: Unicharm Corporation, Ehime (JP)

(72) Inventors: Takuya Miyama, Kanonji (JP); Satoru Sakaguchi, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 16/481,340

(22) PCT Filed: Dec. 19, 2017

(86) PCT No.: PCT/JP2017/045492
§ 371 (c)(1),
(2) Date: Jul. 26, 2019

(87) PCT Pub. No.: WO2018/139114
PCT Pub. Date: Aug. 2, 2018

(65) Prior Publication Data
US 2020/0022849 A1   Jan. 23, 2020

(30) Foreign Application Priority Data
Jan. 26, 2017   (JP) .................................. 2017-012426

(51) Int. Cl.
*A61F 13/15*   (2006.01)
*A61F 13/20*   (2006.01)
(Continued)

(52) U.S. Cl.
CPC .... *A61F 13/51405* (2013.01); *A61F 13/4942* (2013.01); *A61F 13/515* (2013.01);
(Continued)

(58) Field of Classification Search
CPC .............. A61F 13/49406; A61F 13/494; A61F 13/49446; A61F 13/514; B32B 2255/00;
(Continued)

(56) References Cited

U.S. PATENT DOCUMENTS 4,103,062 A * 7/1978 Aberson ................. A61F 13/15
                                                            442/417
4,333,462 A * 6/1982 Holtman ............... A61F 13/535
                                                            604/368
(Continued)

FOREIGN PATENT DOCUMENTS

JP      H04-343764 A     11/1992
JP      2004-256939 A     9/2004
(Continued)

OTHER PUBLICATIONS

International Search Report issued in corresponding International Application No. PCT/JP2017/045492 dated Mar. 20, 2018 (2 pages).
(Continued)

*Primary Examiner* — Michele M Kidwell
(74) *Attorney, Agent, or Firm* — Osha Liang LLP (57) ABSTRACT

A disposable absorbent article, having a front-back direction that is perpendicular to a width direction and a thickness direction that extends from a skin contact surface side to a non-skin contact surface side of a wearer, includes: an absorbent constituent; a liquid-permeable topsheet that is disposed on the skin contact surface side of the absorbent constituent; and a leakage-preventing sheet that is disposed on at least one of an outside, in the thickness direction, of the absorbent constituent, and an outside, in the width direction, of the absorbent constituent. The leakage-preventing sheet includes a water repelling layer including a nonwoven fabric. The nonwoven fabric of the water repelling layer includes fiber and has an average fiber diameter of 0.5 to 10 µm. The water repelling layer includes a water repelling section where a group of particles adhere to a surface of the fiber.

13 Claims, 4 Drawing Sheets

(51) Int. Cl.
  *A61F 13/514* (2006.01)
  *A61F 13/494* (2006.01)
  *A61F 13/515* (2006.01)
  *A61F 13/513* (2006.01)

(52) U.S. Cl.
  CPC .............. *A61F 13/51456* (2013.01); *A61F 2013/51355* (2013.01); *A61F 2013/51452* (2013.01)

(58) Field of Classification Search
  CPC ............ B32B 2255/02; B32B 2255/04; B32B 2260/023; B32B 2260/046
  See application file for complete search history.

(56) References Cited

U.S. PATENT DOCUMENTS

| | | | | |
|---|---|---|---|---|
| 4,373,519 A * | 2/1983 | Errede | ............... | A61F 13/00046 128/DIG. 21 |
| 4,500,315 A * | 2/1985 | Pieniak | ................. | A61F 13/534 604/379 |
| 4,540,454 A * | 9/1985 | Pieniak | ................. | A61F 13/534 156/296 |
| 4,983,245 A * | 1/1991 | Schaefer | ................. | B05D 7/12 156/231 |
| 5,021,050 A * | 6/1991 | Iskra | ................. | A61F 13/53713 604/368 |
| 5,134,007 A * | 7/1992 | Reising | ................. | A61F 13/535 428/134 |
| 5,147,343 A * | 9/1992 | Kellenberger | ........ | A61F 13/531 604/368 |
| 5,192,606 A * | 3/1993 | Proxmire | .......... | A61F 13/49009 428/171 |
| 5,221,573 A * | 6/1993 | Baigas, Jr. | ............. | D04H 1/593 2/243.1 |
| 5,763,331 A * | 6/1998 | Demhartner | .......... | A61F 13/534 442/393 |
| 6,028,016 A * | 2/2000 | Yahiaoui | ............. | A61F 13/8405 442/118 |
| 8,962,139 B2 * | 2/2015 | Zenitani | ............... | G03G 9/0812 423/335 |
| 9,566,198 B2 * | 2/2017 | Wright | ............. | A61F 13/15658 |
| 10,537,483 B2 * | 1/2020 | Li | ....................... | A61F 13/5616 |
| 2003/0186043 A1 * | 10/2003 | Koslow | ............ | A61F 13/15658 428/306.6 |
| 2005/0054255 A1 * | 3/2005 | Morman | ................... | B32B 5/26 442/381 |
| 2006/0004334 A1 * | 1/2006 | Schlinz | ................. | A61F 13/534 604/366 |
| 2011/0270204 A1 * | 11/2011 | Fukudome | ............ | A61F 13/534 604/365 |
| 2012/0203191 A1 * | 8/2012 | Maruo | .................... | A61F 13/49 604/372 |
| 2015/0283000 A1 * | 10/2015 | Faulks | .............. | A61F 13/51104 604/385.101 |
| 2017/0257643 A1 * | 9/2017 | Hu | ......................... | H04N 19/61 |

FOREIGN PATENT DOCUMENTS

| | | |
|---|---|---|
| JP | 2007-523272 A | 8/2007 |
| JP | 2012-518495 A | 8/2012 |
| JP | 2016-108714 A | 6/2016 |

OTHER PUBLICATIONS

Written Opinion issued in the corresponding International Application No. PCT/JP2017/045492 dated Mar. 20, 2018 (3 pages).

* cited by examiner

DISPOSABLE ABSORBENT ARTICLE WITH WATER REPELLING LAYER

TECHNICAL FIELD

The present invention generally relates to a disposable absorbent article that includes a leakage-preventing sheet.

BACKGROUND

A conventional disposable absorbent article that includes nonwoven fabric a surface of which is coated with hydrophobic surface coating is known (see Patent Literature 1, for example).

Patent Literature 1: JP 2012-518495 A

The hydrophobic surface coating of Patent Literature 1 includes at least two kinds of silicone polymers. A surface tension (surface free energy) of silicone is generally 16 to 30 MN/m, a surface tension of water is 73 MN/m, and a surface tension of oil is 25 to 30 MN/m. The larger a difference between a surface tension of silicone and a surface tension of water, the larger water-repellent property (that is, more water is repelled).

Therefore, nonwoven fabric used in the disposable absorbent article disclosed in Patent Literature 1 has a good water-repellent property for urine, but may not have a good oil-repellent property for loose stool that includes oil. Therefore, loose stool pass through nonwoven fabric of the disposable absorbent article of Patent Literature 1, and oozes out.

SUMMARY

One or more embodiments provide a disposable absorbent article that has a good water-repellent property for urine and a good oil-repellent property for loose stool.

A disposable absorbent article according to one or more embodiments includes: a front-back direction and a width direction that are perpendicular to each other; a thickness direction that extends from a skin contact surface side to a non-skin contact surface side of a wearer; an absorbent constituent; a top sheet that is disposed on the skin contact surface side of the absorbent constituent and is liquid-permeable; and a leakage-preventing sheet that is disposed on at least one of an outside, in the thickness direction, of the absorbent constituent, and an outside, in the width direction, of the absorbent constituent, and the leakage-preventing sheet includes a water repelling layer that is made of nonwoven fabric that has an average diameter of fiber of 0.5 to 10 μm, the water repelling layer includes a water repelling section where a group of particles adhere to a surface of the fiber, and the group of particles include first particles that have an average particle size of 1 to 20 μm, and second particles that adhere to surfaces of the first particles and have an average particle size of 5 to 100 nm.

DETAILED DESCRIPTION

At least following matters become apparent with reference to the present description and the attached drawings.

A disposable absorbent article includes:

a front-back direction and a width direction that are perpendicular to each other;

a thickness direction that extends from a skin contact surface side to a non-skin contact surface side of a wearer;

an absorbent constituent;

a top sheet that is disposed on the skin contact surface side of the absorbent constituent and is liquid-permeable; and a leakage-preventing sheet that is disposed on at least one of an outside, in the thickness direction, of the absorbent constituent, and an outside, in the width direction, of the absorbent constituent, and the leakage-preventing sheet includes a water repelling layer that is made of nonwoven fabric that has an average diameter of fiber of 0.5 to 10 μm, the water repelling layer includes a water repelling section where a group of particles adhere to a surface of the fiber, and the group of particles include first particles that have an average particle size of 1 to 20 μm, and second particles that adhere to surfaces of the first particles and have an average particle size of 5 to 100 nm.

The water repelling layer of the leakage-preventing sheet is made of nonwoven fabric that has an average diameter of fiber of 0.5 to 10 μm. Since the average diameter of fiber is 0.5 to 10 μm, the fiber is easily closely disposed, and thus urine and loose stool are less likely to pass through gaps between the fiber. Further, the water repelling layer includes the water repelling section where the group of particles adhere to a surface of the fiber. The group of particles include the first particles that have an average particle size of 1 to 20 μm, and the second particles that adhere to surfaces of the first particles and have an average particle size of 5 to 100 nm. Consequently, the first particles form projections and depressions on a surface of the fiber of the water repelling layer. The second particles form projections and depressions on surfaces of the first particles. The particles that have different particle sizes form two levels of projections and depressions. Therefore, urine and loose stool touches the group of particles that adhere to a surface of the fiber when urine and loose stool is passing through between the fiber. Consequently, urine and loose stool are less likely to pass through gaps between the fiber to which the group of particles adhere. Therefore, the leakage-preventing sheet has a good water-repellent property for urine and a good oil-repellent property for loose stool.

In the absorbent article according to one or more embodiments, the leakage-preventing sheet has a protective layer that is disposed on an outside, in the thickness direction, of the water repelling layer, and the protective layer is made of nonwoven fabric that has an average diameter of fiber of 10 μm or more.

In such an absorbent article, the protective layer protects an outer surface, in the thickness direction, of the water repelling layer. Therefore, a shape of the group of particles in the water repelling layer is easily maintained. Even if a surface of the leakage-preventing sheet is scraped during circulation or usage, the water repelling layer maintains water-repellent performance, and has a good water-repellent property for urine and a good oil-repellent property for loose stool. Further, an average diameter of the fiber that forms the protective layer is 10 μm or more, and thus is larger than an average diameter of the fiber of the water repelling layer. Consequently, the fiber of the protective layer is likely to be more sparsely disposed than the fiber of the water repelling layer. The protective layer is more elastic than the water repelling layer. Therefore, structure of the group of particles of the water repelling layer is easily protected by the protective layer. Since the fiber of the protective layer is more sparsely disposed than the fiber of the water repelling layer, the protective layer is likely to attract urine and loose stool. In the leakage-preventing sheet configured in this way, the protective layer rapidly attracts urine and loose stool, the attracted body fluid is less likely to pass through the water repelling layer, and is retained in the water repelling layer. More body fluid is attracted, and leakage of the body fluid is restricted. Therefore, the absorbent article is more comfortable.

In the absorbent article according to one or more embodiments, at least part of the water repelling section is disposed at a central portion of the water repelling layer, the water repelling layer is equally divided, in the thickness direction, into three portions, and the central portion is a central portion, in the thickness direction, of the three portions of the water repelling layer.

In such an absorbent article, a portion that is on an outside, in the thickness direction, of the central portion, protects an outer surface, in the thickness direction, of the central portion. Therefore, a shape of the group of particles in the central portion is easily maintained. Even if a surface of the water repelling layer is scraped during circulation or usage, the central portion of the water repelling layer maintains water-repellent performance, and has a good water-repellent property for urine and a good oil-repellent property for loose stool.

In the absorbent article according to one or more embodiments, at least one of the topsheet and a backsheet that is disposed on the non-skin contact surface side of the absorbent constituent includes a section that includes projections and depressions between the projections, and the projections project toward the skin contact surface side, and the section that includes projections and depressions is disposed over the water repelling section in the thickness direction.

When an external force acts on such an absorbent article, projections and depressions in the section that includes projections and depressions deform, and thus transmission of the external force to the leakage-preventing sheet is restricted. Since the section that includes projections and depressions is disposed over the water repelling section, a shape of the group of particles in the water repelling section is easily maintained. Therefore, the leakage-preventing sheet has a good water-repellent property for urine and a good oil-repellent property for loose stool.

In the absorbent article according to one or more embodiments, the top sheet and the backsheet that each include the section that includes projections and depressions are discontinuously bonded to the leakage-preventing sheet.

Such an absorbent article includes a portion where the sheet that includes the section that includes projections and depressions is bonded to the leakage-preventing sheet, and a portion where the sheet that includes the section that includes projections and depressions is not bonded to the leakage-preventing sheet. The portion where the sheet that includes the section that includes projections and depressions is not bonded to the leakage-preventing sheet is more likely to deform than the portion where the sheet that includes the section that includes projections and depressions is bonded to the leakage-preventing sheet. Therefore, when an external force acts on the absorbent article, the portion where the sheet that includes the section that includes projections and depressions is not bonded to the leakage-preventing sheet absorbs the external force, and thus transmission of the external force to the leakage-preventing sheet is restricted. Therefore, a shape of the group of particles in the water repelling layer is easily maintained. A good water-repellent property for urine and a good oil-repellent property for loose stool are provided.

In the absorbent article according to one or more embodiments, the water repelling section may be disposed on the non-skin contact surface side of the absorbent constituent to cover the whole absorbent constituent.

In such an absorbent article, the water repelling section is disposed to cover the whole non-skin contact surface of the absorbent constituent, and the water repelling section has a water-repellent property on the non-skin contact surface side of the absorbent constituent. The leakage-preventing sheet surely has a water-repellent property on the non-skin contact surface side of the absorbent constituent, and thus an absorbent article that does not include a backsheet is provided. A backsheet of an absorbent article is generally made of film, and thus is less flexible than a leakage-preventing sheet made of nonwoven fabric. Therefore, the backsheet may be uncomfortable and make rustling when the backsheet deforms. An absorbent article that does not include a backsheet is less uncomfortable and reduces rustling when the absorbent article deforms. Therefore, the absorbent article that does not include a backsheet is more comfortable.

In the absorbent article according to one or more embodiments, the water repelling section is disposed on the non-skin contact surface side of the absorbent constituent to cover a portion of the absorbent constituent that is at a rear side of a center, in the front-back direction, of the disposable absorbent article.

The rear side of a center, in the front-back direction, is pressed against a rear side of a crotch of a body. Stool is excreted to the rear side of a center, in the front-back direction. In such an absorbent article, the water repelling section is disposed to cover the portion of the absorbent constituent that is at a rear side of a center, in the front-back direction, and thus the water repelling section prevents leakage of stool. The leakage-preventing sheet surely prevents leakage on the non-skin contact surface side of the absorbent constituent, and thus an absorbent article that does not include a backsheet is provided. The backsheet is generally made of film, and thus is less flexible than the leakage-preventing sheet made of nonwoven fabric. Therefore, the backsheet may be uncomfortable and make rustling when the backsheet deforms. An absorbent article that does not include a backsheet is less uncomfortable and reduces rustling when the absorbent article deforms. Therefore, the absorbent article that does not include a backsheet is more comfortable.

In the absorbent article according to one or more embodiments, a basis weight of the group of particles of the water repelling layer is larger than a basis weight of the group of particles of the protective layer.

In such an absorbent article, a basis weight of the group of particles of the water repelling layer is large. Therefore, many groups of particles maintain shape in the water repelling layer protected by the protective layer. Consequently, the water repelling layer has a good water-repellent property and a good oil-repellent property.

In the absorbent article according to one or more embodiments, a distance between the fiber of the water repelling layer is 50 μm or less.

In such an absorbent article, urine and loose stool are less likely to pass through gaps between the fiber. Consequently, the leakage-preventing sheet is more likely to prevent leakage.

In the absorbent article according to one or more embodiments, a contact angle of the water repelling layer relative to water and oil is 135° or more.

In such an absorbent article, the water repelling layer has a contact angle of 135° or more relative to water and oil. Therefore, the water repelling layer has a good water-repellent property and a good oil-repellent property.

In the absorbent article according to one or more embodiments, a surface tension of the water repelling layer is 30 mN/m or less.

In such an absorbent article, a difference between a surface tension of the water repelling layer and a surface tension of water is large, and a difference between a surface tension of the water repelling layer and a surface tension of oil is large. Therefore, the water repelling layer satisfactorily prevents leakage of urine and loose stool.

In the absorbent article according to one or more embodiments, the leakage-preventing sheet constitutes at least one of an uprising gather and a leg gather.

In such an absorbent article, a film that prevents leakage does not constitute an uprising gather and a leg gather, but nonwoven fabric constitutes the uprising gather and the leg gather. The nonwoven fabric prevents leakage of urine and loose stool. The uprising gather and the leg gather are disposed to be in contact with skin of a wearer, and are made of nonwoven fabric. Therefore, the uprising gather and the leg gather are softly in contact with skin, and thus are more comfortable.

Next, a disposable diaper 10 as an example of a disposable absorbent article according to one or more embodiments will be described with reference to the drawings. Disposable absorbent articles according to one or more embodiments are not limited to a disposable diaper, but include absorbent pads attached to underwear or diapers. In the description about the drawings, the same or similar portions are designated as the same or similar reference symbols. However, the drawings are schematic. Note that a ratio of dimensions is different from an actual ratio of dimensions. Therefore, concrete dimensions should be determined by referring to the description described later. A relation or ratio of dimensions in some portions may be different between the drawings.

(1) Whole Schematic Configuration of Disposable Diaper

Figure 1:
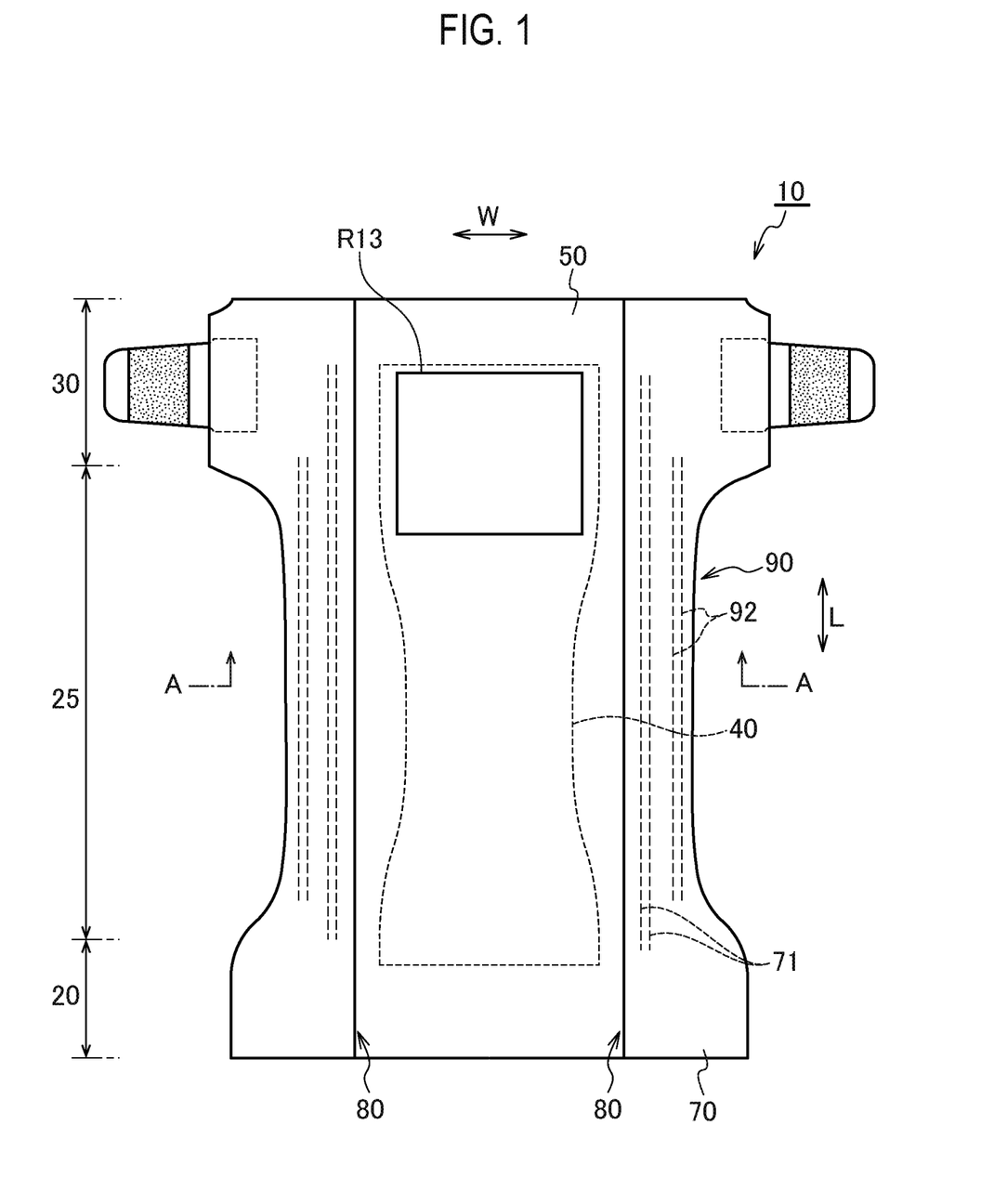
FIG. 1 is an exploded plan view of a disposable diaper according to one or more embodiments.
Figure 2:
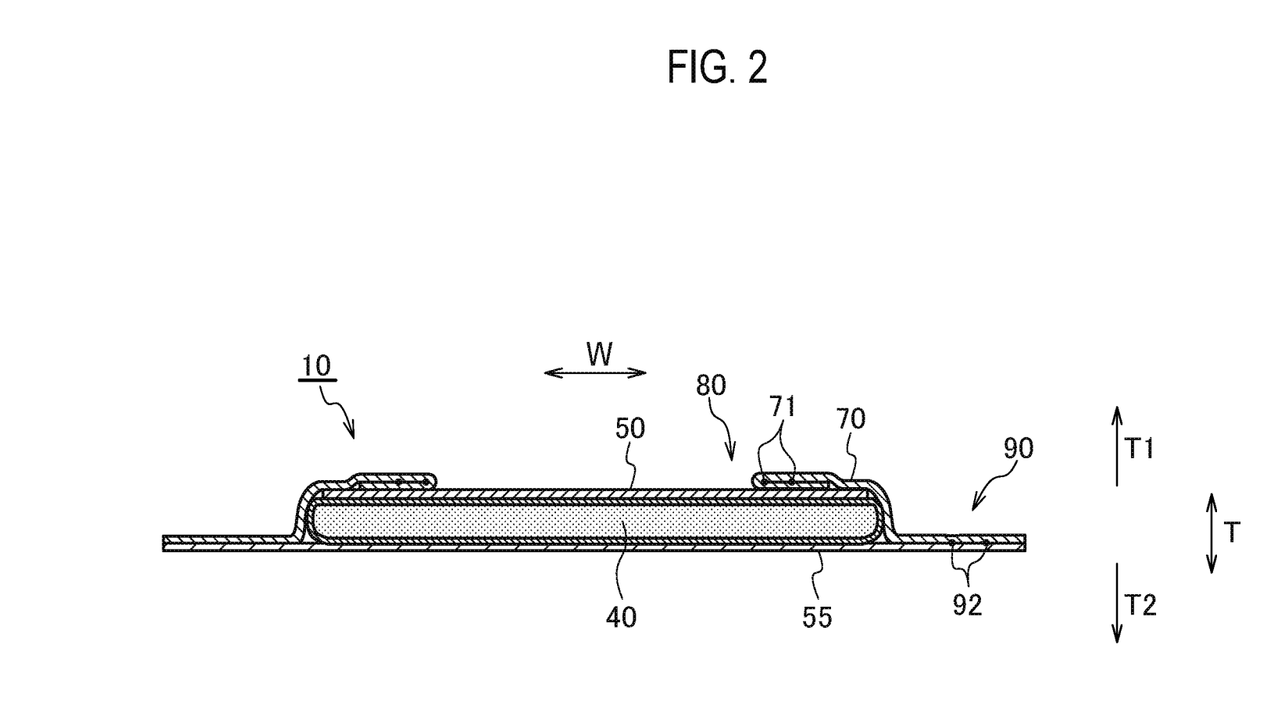
FIG. 2 is a cross-sectional view taken along line A-A in FIG. 1.

FIG. 1 is an exploded plan view of a disposable diaper 10 according to one or more embodiments. The exploded plan view illustrated in FIG. 1 illustrates a condition in which elastic portions of uprising gathers are stretched. In the condition, wrinkles are not formed in a topsheet 50 and side sheets 70, for example, that constitute the disposable diaper. FIG. 2 is a cross-sectional view taken along line A-A in FIG. 1.

The disposable diaper 10 includes a front waistline region 20, a crotch region 25, and a rear waistline region 30. The front waistline region 20 is in contact with a front waist (belly) of a wearer. The rear waistline region 30 is in contact with a rear waist (back) of a wearer. The crotch region 25 is between the front waistline region 20 and the rear waistline region 30. In one or more embodiments, a direction from the front waistline region 20 to the rear waistline region 30 is designated as a front-back direction L, a direction perpendicular to the front-back direction L is designated as a width direction W, and a direction that extends from a skin contact surface side T1 to a non-skin contact surface side T2 of a wearer is designated as a thickness direction T.

The disposable diaper 10 includes an absorbent constituent 40. The absorbent constituent 40 extends across the crotch region 25 to at least one of the front waistline region 20 and the rear waistline region 30. In one or more embodiments, the absorbent constituent 40 is disposed across the front waistline region 20, the crotch region 25, and the rear waistline region 30. The absorbent constituent 40 includes an absorbent core that contains absorbent material, such as pulp and super-absorbent polymer (SAP).

The top sheet 50 that is liquid-permeable is on a skin contact surface side T1 of the absorbent constituent 40. The topsheet 50 forms a skin contact surface of the disposable diaper 10, and is in contact with a wearer. The topsheet 50 is disposed across the front waistline region 20, the crotch region 25, and the rear waistline region 30. The topsheet 50 includes fiber. Concretely, the topsheet 50 is made of nonwoven fabric.

The topsheet 50 includes an attracting section R13. The attracting section R13 attracts more loose-stool to an absorbent-constituent side than a section around the attracting section R13 attracts. Concretely, for example, the attracting section R13 includes a section that includes an opening that extends in the thickness direction T, and a section that includes projections and depressions that are alternately formed. The projections project toward the skin contact surface side. The attracting section R13 that includes the opening attracts loose stool on a skin contact surface of the topsheet to a non-skin contact surface side of the topsheet through the opening. The attracting section that includes the projections and the depressions retains loose stool in the depressions between the projections, and rapidly directs the loose stool in the depressions to a non-skin contact surface side. In the attracting section in which the projections have a shape like a grid, the grid-like projections surround the depressions, and restrict spread of loose stool to around the depressions. Consequently, loose stool in the depressions is rapidly directed to the non-skin contact surface side. The attracting section is disposed over a water repelling section in the thickness direction. The water repelling section will be described later. The attracting section is disposed at a rear side of a center, in the front-back direction, of the absorbent article. More specifically, the attracting section is disposed in the rear waistline region. The attracting section is in a section to which stool is excreted.

A leakage-preventing sheet 55 is disposed on a non-skin contact surface side of the absorbent constituent 40. The leakage-preventing sheet 55 forms a non-skin contact surface of the disposable diaper. The leakage-preventing sheet 55 is water-repellent and oil-repellent. A configuration of the leakage-preventing sheet 55 will be described in detail later.

A pair of uprising gathers 80 are disposed on both sides, in the width direction, of a center, in the width direction, of the disposable diaper 10, respectively. Each uprising gather 80 includes a side sheet 70, and a side elastic member 71 as an elastic member.

The side sheet 70 covers an outer edge of the topsheet. The side elastic member 71 is disposed on an inner edge side of the side sheet 70. The side elastic member 71 is stretchable in the front-back direction. The uprising gather 80 includes an uprising portion that is uprisen toward a wearer by the side elastic member 71 that is stretchable in the front-back direction. The uprising gather 80 forms a wall that uprises toward skin at an outer edge of the absorbent constituent 40. Consequently, the uprising gather 80 prevents leakage of body waste from a side.

Outer edges of the disposable diaper 10 include leg gathers 90, respectively. The leg gathers 90 are disposed around legs of a wearer, respectively. Each leg gather 90 includes the side sheet 70, a leg elastic member 92, and the leakage-preventing sheet 55. The leg elastic member 92 is disposed between the side sheet 70 and the leakage-preventing sheet 55, and extends in the front-back direction. The leg gather 90 is closely in contact with a leg at an outer edge of the absorbent constituent 40. Consequently, the leg gather 90 prevents leakage of body waste from a side.

(2) Detailed Configuration of Leakage-Preventing Sheet

Figure 3:
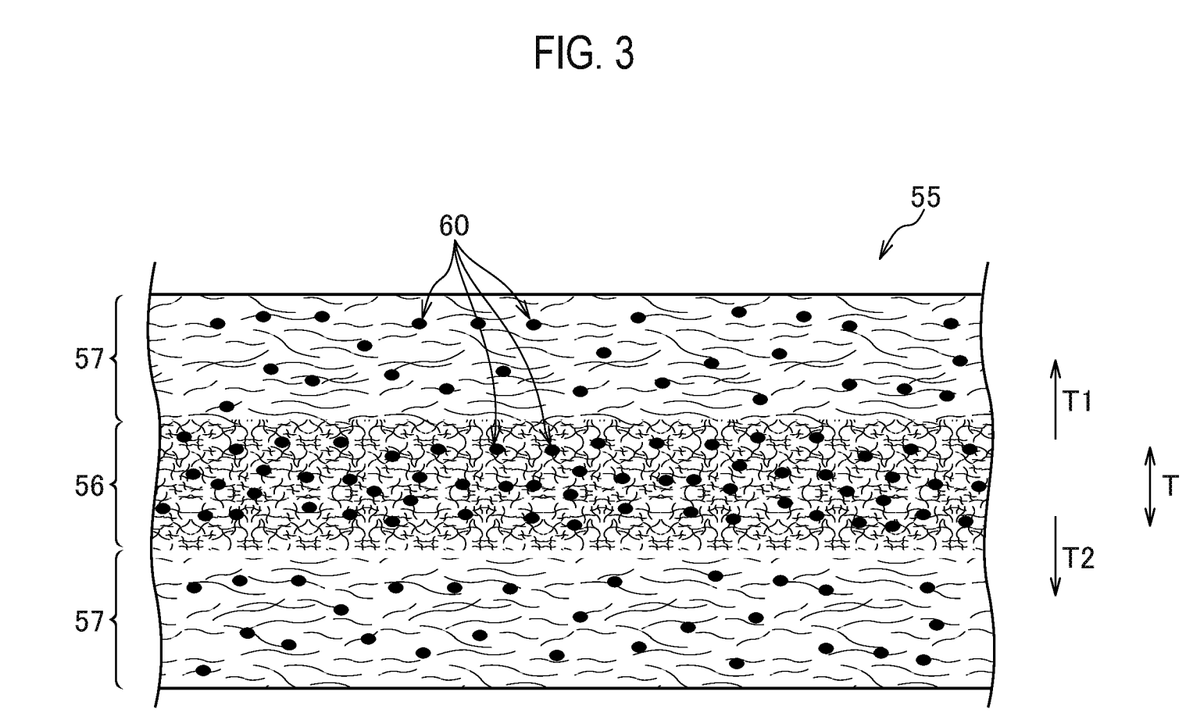
FIG. 3 is a cross-sectional view that schematically illustrates a cross section of a leakage-preventing sheet according to one or more embodiments.

Next, the leakage-preventing sheet 55 will be described. FIG. 3 is a cross-sectional view that schematically illustrates the leakage-preventing sheet. The leakage-preventing sheet 55 is disposed on the non-skin contact surface side T2, that is on an outside, in the thickness direction T, of the absorbent constituent 40. The leakage-preventing sheet 55 may be disposed on the skin contact surface side T1 of the absorbent constituent 40. Further, the leakage-preventing sheet 55 may be disposed on outside, in the width direction W, of the absorbent constituent 40.

As illustrated in FIG. 3, the leakage-preventing sheet 55 includes three layers: a water repelling layer 56, a protective layer 57 on the skin contact surface side T1 of the water repelling layer 56, and a protective layer 57 disposed on the non-skin contact surface side T2 of the water repelling layer 56. The leakage-preventing sheet 55 is made of spunbond-meltblown-spunbond nonwoven fabric. The water repelling layer 56 is made of meltblown nonwoven fabric. The protective layers 57 are made of spunbond nonwoven fabric.

The water repelling layer 56 is at a center, in the thickness direction T, of the leakage-preventing sheet 55. Fiber of the water repelling layer 56 contains at least one of polypropylene and polyethylene terephthalate. A basis weight of the fiber of the water repelling layer 56 is 12 gsm. An average diameter of the fiber is 0.5 to 10 μm. A distance between the fiber of the water repelling layer 56 is 50 μm or less.

The water repelling layer 56 includes a water repelling section where a group of particles 60 adhere to a surface of the fiber. In one or more embodiments, the water repelling section extends over the whole water repelling layer 56 in a plan view. In one or more embodiments, the water repelling section is over the absorbent constituent 40. Further, the water repelling section may not be at outer edges of the disposable diaper 10. Further, the water repelling section may not be at a front edge and a rear edge of the disposable diaper 10. The water repelling section may be disposed on the non-skin contact surface side T2 of the absorbent constituent 40 to cover a portion of the absorbent constituent 40 that is at a rear side of a center, in the front-back direction, of the absorbent article. The water repelling section may be disposed over the attracting section R13 of the topsheet 50.

Figure 4:
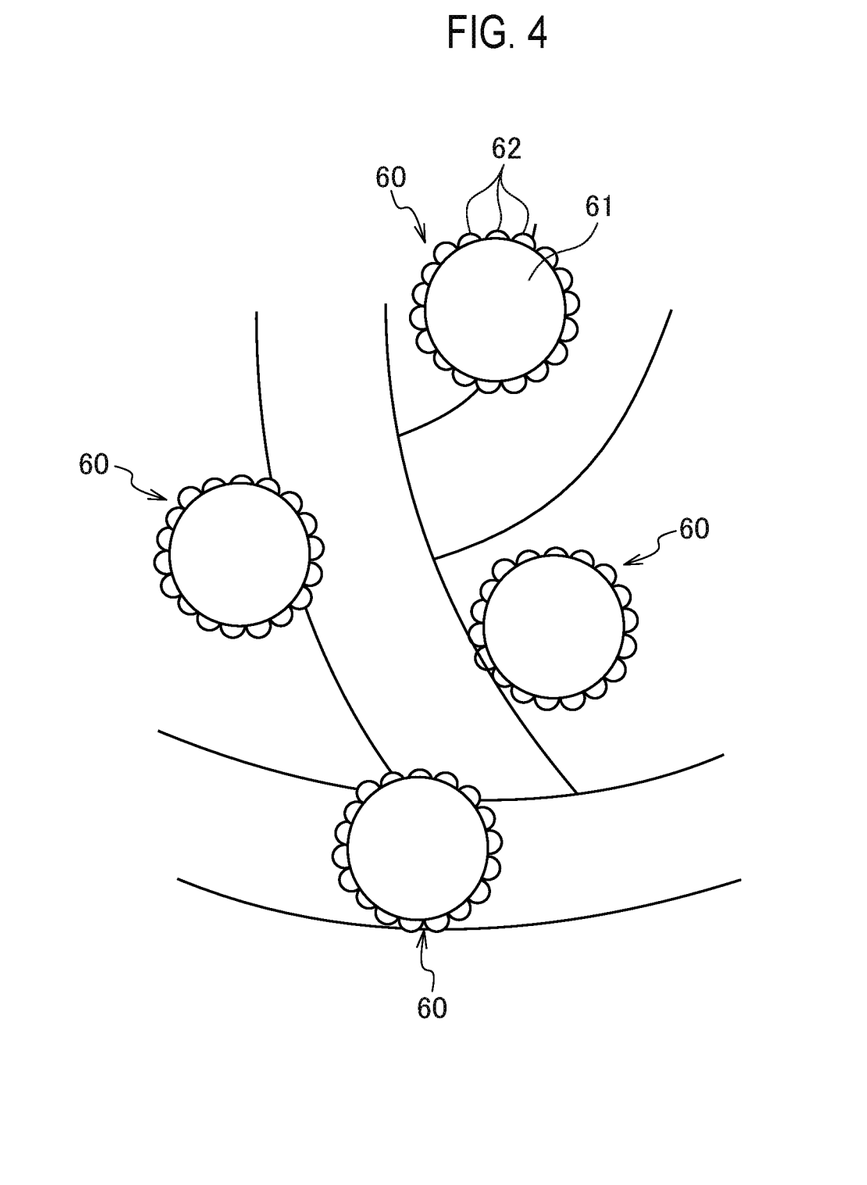
FIG. 4 schematically illustrates structure of a group of particles and fiber according to one or more embodiments.

As illustrated in FIG. 4, the group of particles 60 include first particles 61 that have an average particle size of 1 to 20 μm, and second particles 62 that adhere to surfaces of the first particles 61 and have an average particle size of 5 to 100 nm. For example, the first particles 61 are resin particles that are made of olefin-based resin. For example, the second particles 62 are oxide particles. The second particles are dispersed on surfaces of the first particles 61 and adhere to the a surfaces of the first particles 61. The first particles 61 form minute projections and depressions on a surface of fiber that forms the water repelling layer 56. The second particles 62 form minute projections and depressions on surfaces of the minute projections and depressions. Such a shape of the surface improves water-repellent property and oil-repellent property of the surfaces.

An average particle size of the particles is measured with a scanning electron microscope (FE-SEM). If a scanning electron microscope has a low resolution, another electron microscope, such as a transmission electron microscope, may be used in addition to the scanning electron microscope. Concretely, 20 particles are randomly selected by observation with a scanning electron microscope or the like. An average of diameters of the 20 particles is used as an average particle size of primary particles. The diameters are diameters of particles if the particles are spherical. The diameters are each an average of a longest diameter and a shortest diameter of each particle if the particles are not spherical.

Methods that allow the first particles 61 and the second particles 62 to adhere to a surface of fiber are not particularly limited. For example, paint is made by dispersing the first particles 61 and the second particles 62 in a solvent. The paint is applied to nonwoven fabric and dried. Consequently, a film of the first particles 61 is formed. Further, the second particles 62 are dispersed on a surface of the film and adhere to the surface of the film.

The protective layers 57 are on both outsides, in the thickness direction T, of the water repelling layer 56. Fiber of the protective layers 57 contains at least one of polypropylene and polyethylene terephthalate. Fiber of the protective layers 57 has a basis weight of 6 gsm and an average diameter of 12 to 22 μm. In one or more embodiments, the average diameter of fiber of the protective layers 57 is 10 μm or more, and is larger than an average diameter of fiber of the water repelling layer 56. The group of particles 60 adhere to a surface of fiber that forms the water repelling layer 56. A configuration of the group of particles 60 is similar to a configuration of the group of particles of the water repelling layer 56.

A basis weight of the group of particles 60 of the water repelling layer 56 is larger than a basis weight of the group of particles 60 of the protective layers 57. In one or more embodiments, a basis weight of the group of particles 60 of the water repelling layer 56 is 2 gsm, and a basis weight of the group of particles of the protective layers 57 is 1 gsm.

In one or more embodiments, a surface tension of the water repelling layer 56 is 30 mN/m or less, and a surface tension of the leakage-preventing sheet 55 that includes the protective layers 57 is 30 mN/m or less. In one or more embodiments, the surface tension of the water repelling layer 56 is 20 mN/m or less, and the surface tension of the leakage-preventing sheet 55 that includes the protective layers 57 is 20 mN/m or less. Surface tensions are measured with an Automatic Surface Tensiometer CBVP-Z (manufactured by Kyowa Interface Science Co., Ltd.) at 25° C. In one or more embodiments, a contact angle of the water repelling layer 56 relative to water and oil is 135° or more. Further, a contact angle of the leakage-preventing sheet 55 that includes the protective layers 57 may be 135° or more. A surface disposed on the non-skin contact surface side is used to measure a contact angle relative to purified water and oil. The contact angle is measured with a contact-angle measuring instrument (a solid-liquid-interface analyzing instrument "Drop Master300" manufactured by Kyowa Interface Chemicals company).

(3) Other Embodiments

In the above-described embodiments, the leakage-preventing sheet includes the protective layers. However, a leakage-preventing sheet according to one or more embodiments may not include the protective layers. In one or more embodiments, at least part of a water repelling section is disposed at a central portion of a water repelling layer if a leakage-preventing sheet does not include protective layers. The water repelling layer is equally divided, in the thickness direction, into three portions. The central portion is a central portion, in the thickness direction, of the three portions of the water repelling layer.

An absorbent article may include a backsheet on a non-skin contact surface side of a leakage-preventing sheet. The backsheet includes a non-skin contact surface of the absorbent article, and is on a non-skin contact surface side of an absorbent constituent and the leakage-preventing sheet. The backsheet may include a section that includes projections and depressions. Further, the backsheet that includes the section that includes projections and depressions may be discontinuously bonded to the leakage-preventing sheet. Concretely, a section where the leakage-preventing sheet is bonded to the backsheet and a section where the leakage-preventing sheet is not bonded to the backsheet may be alternately disposed between the leakage-preventing sheet and the backsheet. If a topsheet that includes a section that includes projections and depressions is over a leakage-preventing sheet in a thickness direction, the topsheet may be discontinuously bonded to the leakage-preventing sheet.

Embodiments of the present invention are disclosed above. However, it should not be thought that discussion and the drawings that form part of the disclosure limit the present invention. Based on the disclosure, various alternative embodiments, examples, and applied techniques are obvious to a person skilled in the art. Therefore, a technical scope of the present invention is defined only by matters specifying the invention that are related to a scope of claims that is appropriate based on the above description.

Provided is a disposable absorbent article that has a good water-repellent property for urine and a good oil-repellent property for loose stool.

10 disposable diaper (disposable absorbent article)
40 absorbent constituent
50 top sheet
55 leakage-preventing sheet
56 water repelling layer
57 protective layer
60 group of particles
61 first particle
62 second particle
80 uprising gather
90 leg gather
R13 attracting section

The invention claimed is:

1. A disposable absorbent article having a front-back direction that is perpendicular to a width direction and a thickness direction that extends from a skin contact surface side to a non-skin contact surface side of a wearer, wherein the disposable absorbent article comprises:
   an absorbent constituent;
   a liquid-permeable topsheet that is disposed on the skin contact surface side of the absorbent constituent; and
   a leakage-preventing sheet that is disposed on at least one of an outside, in the thickness direction, of the absorbent constituent, and an outside, in the width direction, of the absorbent constituent, wherein
   the leakage-preventing sheet includes a water repelling layer comprising a nonwoven fabric,
   the nonwoven fabric of the water repelling layer comprises fiber and has an average fiber diameter of 0.5 to 10 µm,
   the water repelling layer includes a water repelling section where a group of particles adhere to a surface of the fiber, and
   the group of particles includes:
      first particles that have an average particle size of 1 to 20 µm; and
      second particles that adhere to surfaces of the first particles and that have an average particle size of 5 to 100 nm.

2. The disposable absorbent article according to claim 1, wherein
   the leakage-preventing sheet has a protective layer that is disposed on an outside, in the thickness direction, of the water repelling layer, and
   the protective layer comprises a nonwoven fabric that has an average fiber diameter of 10 µm or more.

3. The disposable absorbent article according to claim 1, wherein
   at least part of the water repelling section is disposed at a central portion of the water repelling layer,
   the water repelling layer is equally divided, in the thickness direction, into three portions, and
   the central portion is disposed in a center in the thickness direction of the three portions of the water repelling layer.

4. The disposable absorbent article according to claim 1, wherein
   at least one of the topsheet and a backsheet that is disposed on the non-skin contact surface side of the absorbent constituent includes a section that includes projections and depressions that are disposed between the projections,
   the projections project toward the skin contact surface side, and
   the section that includes the projections and the depressions is disposed over the water repelling section in the thickness direction.

5. The disposable absorbent article according to claim 4, wherein
   the topsheet and the backsheet each include the section that includes the projections and the depressions, and
   the topsheet and the backsheet are discontinuously bonded to the leakage-preventing sheet.

6. The disposable absorbent article according to claim 1, wherein
   the water repelling section is disposed on the non-skin contact surface side of the absorbent constituent and covers the whole absorbent constituent.

7. The disposable absorbent article according to claim 1, wherein
   the water repelling section is disposed on the non-skin contact surface side of the absorbent constituent and covers a portion of the absorbent constituent that is disposed at a rear side, in the front-back direction, of a center of the disposable absorbent article.

8. The disposable absorbent article according to claim 1, wherein
   the topsheet includes an attracting section that attracts more body waste to an absorbent-constituent side than a section around the attracting section attracts, and
   the attracting section is disposed over the water repelling section in the thickness direction.

9. The disposable absorbent article according to claim 2, wherein
 the protective layer includes a group of particles, and
 a weight of a group of particles of the water repelling layer is larger than a basis weight of a group of particles of the protective layer.

10. The disposable absorbent article according to claim 1, wherein
 a distance between the fibers of the water repelling layer is 50 μm or less.

11. The disposable absorbent article according to claim 1, wherein
 a contact angle of the water repelling layer relative to water and oil is 135° or more.

12. The disposable absorbent article according to claim 1, wherein
 a surface tension of the water repelling layer is 30 mN/m or less.

13. The disposable absorbent article according to 1, wherein
 the leakage-preventing sheet constitutes at least one of an uprising gather and a leg gather.

* * * * *